(12) United States Patent
Ikushima

(10) Patent No.: US 11,117,713 B2
(45) Date of Patent: Sep. 14, 2021

(54) LID FOR LIQUID MATERIAL STORAGE CONTAINER, AND LIQUID MATERIAL STORAGE CONTAINER

(71) Applicant: MUSASHI ENGINEERING, INC., Mitaka (JP)

(72) Inventor: Kazumasa Ikushima, Mitaka (JP)

(73) Assignee: MUSASHI ENGINEERING, INC., Tokyo (JP)

( * ) Notice: Subject to any disclaimer, the term of this patent is extended or adjusted under 35 U.S.C. 154(b) by 124 days.

(21) Appl. No.: 16/497,992

(22) PCT Filed: Mar. 23, 2018

(86) PCT No.: PCT/JP2018/011615
§ 371 (c)(1),
(2) Date: Sep. 26, 2019

(87) PCT Pub. No.: WO2018/180956
PCT Pub. Date: Oct. 4, 2018

(65) Prior Publication Data
US 2020/0039698 A1 Feb. 6, 2020

(30) Foreign Application Priority Data

Mar. 27, 2017 (JP) .............................. JP2017-061714

(51) Int. Cl.
*A61M 5/315* (2006.01)
*B65D 41/28* (2006.01)
*B65D 51/16* (2006.01)

(52) U.S. Cl.
CPC ......... *B65D 41/28* (2013.01); *B65D 51/1688* (2013.01)

(58) Field of Classification Search
CPC .............. B65D 51/1688; B65D 43/021; B65D 43/0204; B65D 43/0208; B65D 43/08;
(Continued)

(56) References Cited

U.S. PATENT DOCUMENTS 7,431,877 B2 * 10/2008 Druitt ................ B65D 41/3447
264/328.1
9,958,067 B2 * 5/2018 Strong ..................... F16J 1/003
(Continued)

FOREIGN PATENT DOCUMENTS

EP 2 777 826 A2 9/2014
GB 1 529 445 A 10/1978
(Continued)

OTHER PUBLICATIONS

International Search Report dated Jun. 12, 2018, issued in counterpart application No. PCT/JP2018/011615. (1 page).
(Continued)

*Primary Examiner* — King M Chu
(74) *Attorney, Agent, or Firm* — Westerman, Hattori, Daniels & Adrian, LLP

(57) ABSTRACT

A lid for a liquid material storage container solves problems of uplift and breakage of the lid, and ensures high efficiency in attachment and detachment operations. The lid includes an upper plate portion covering a flange and a large-diameter opening of a storage cylinder; a plug portion extending downward from a central region of the upper plate portion and plugging the large-diameter opening of the storage cylinder; a pair of first lateral portions coming into contact with lateral surfaces of a pair of short sides of the flange when the lid is closed; a pair of claw portions extending from the pair of first lateral portions toward the plug portion and coming into contact with lower surfaces of the pair of short sides of the flange when the lid is closed; and a push-up operating portion formed in at least one of the pair of first lateral portions.

19 Claims, 11 Drawing Sheets

(58) Field of Classification Search
CPC ... B65D 41/28; A61M 5/31555; A61M 5/204;
A61M 5/31511
USPC .......................................... 220/787; 222/386
See application file for complete search history.

(56) References Cited

U.S. PATENT DOCUMENTS

| | | | |
|---|---|---|---|
| 2005/0209562 A1* | 9/2005 | Kim | A61M 5/14526 604/141 |
| 2007/0287965 A1* | 12/2007 | Strong | B05C 17/00576 604/218 |
| 2012/0022466 A1* | 1/2012 | James | A61M 5/3287 604/198 |
| 2014/0263403 A1 | 9/2014 | Conner et al. | |

FOREIGN PATENT DOCUMENTS

| | | |
|---|---|---|
| JP | S48-24886 A | 3/1973 |
| JP | 2003-175353 A | 6/2003 |
| JP | 2009-539607 A | 11/2009 |
| JP | 4986600 B2 | 7/2012 |

OTHER PUBLICATIONS

International Preliminary Report on Patentability (Form PCT/IB/373) issued in counterpart International application No. PCT/JP2018/011615 dated Oct. 1, 2019 with Form PCT/ISA/237. (6 pages).
Extended Supplementary Search Report dated Dec. 9, 2020, issued in counteprart EP Application No. 18 77 5456.9 (1 page).

* cited by examiner

[Fig.1]
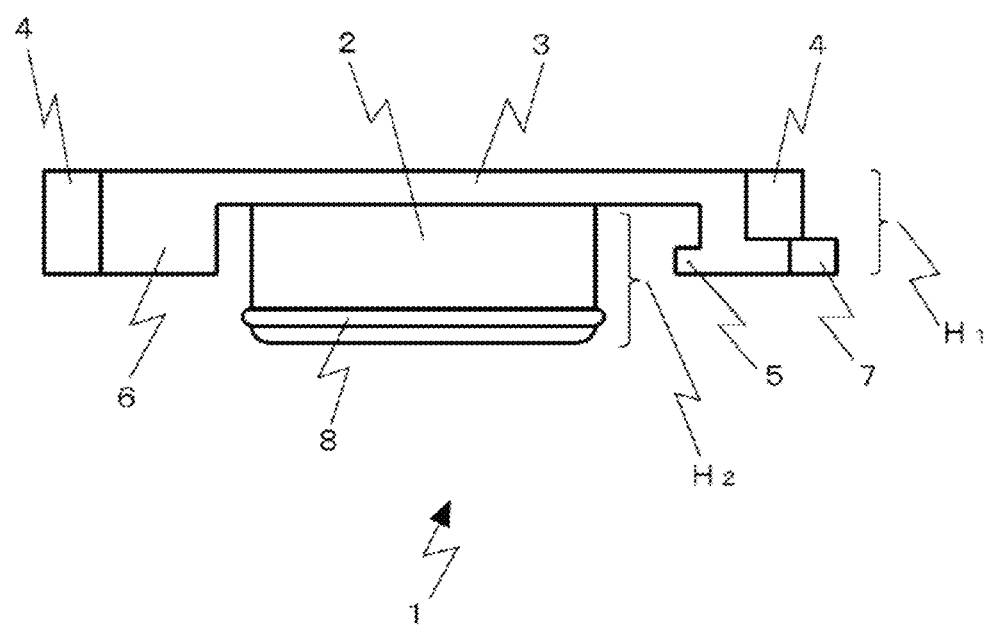

[Fig.2]
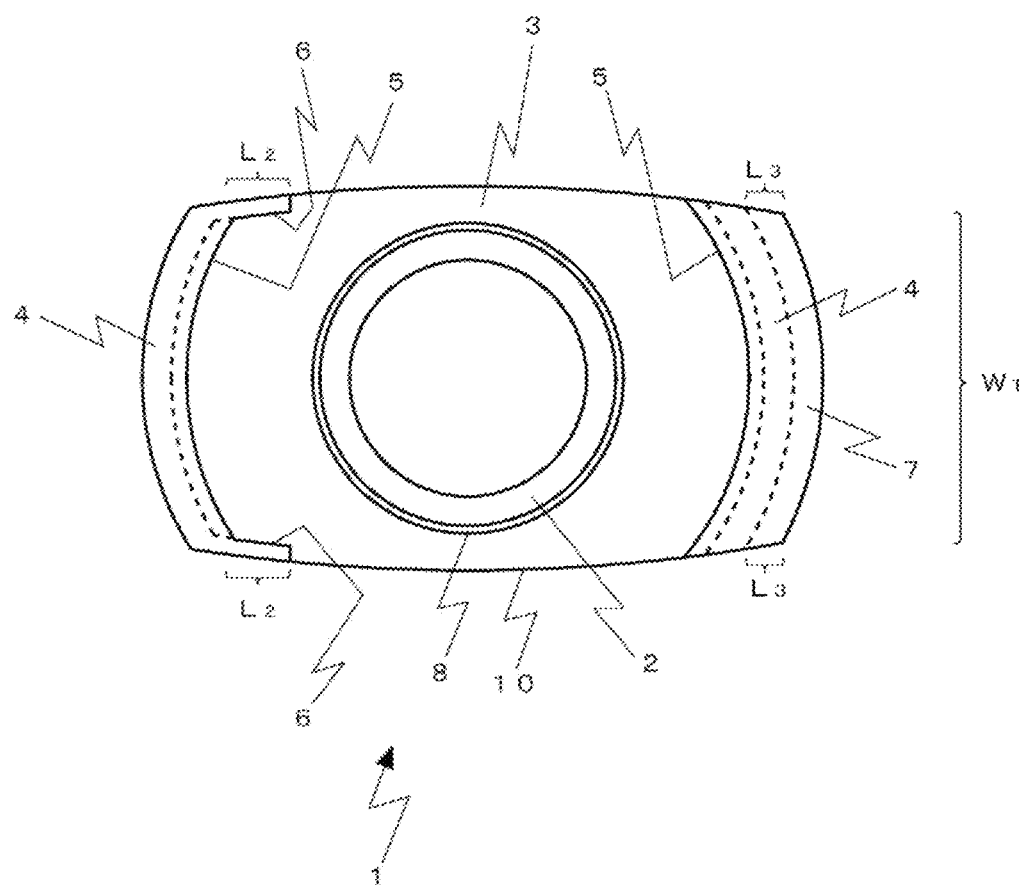

[Fig.3]
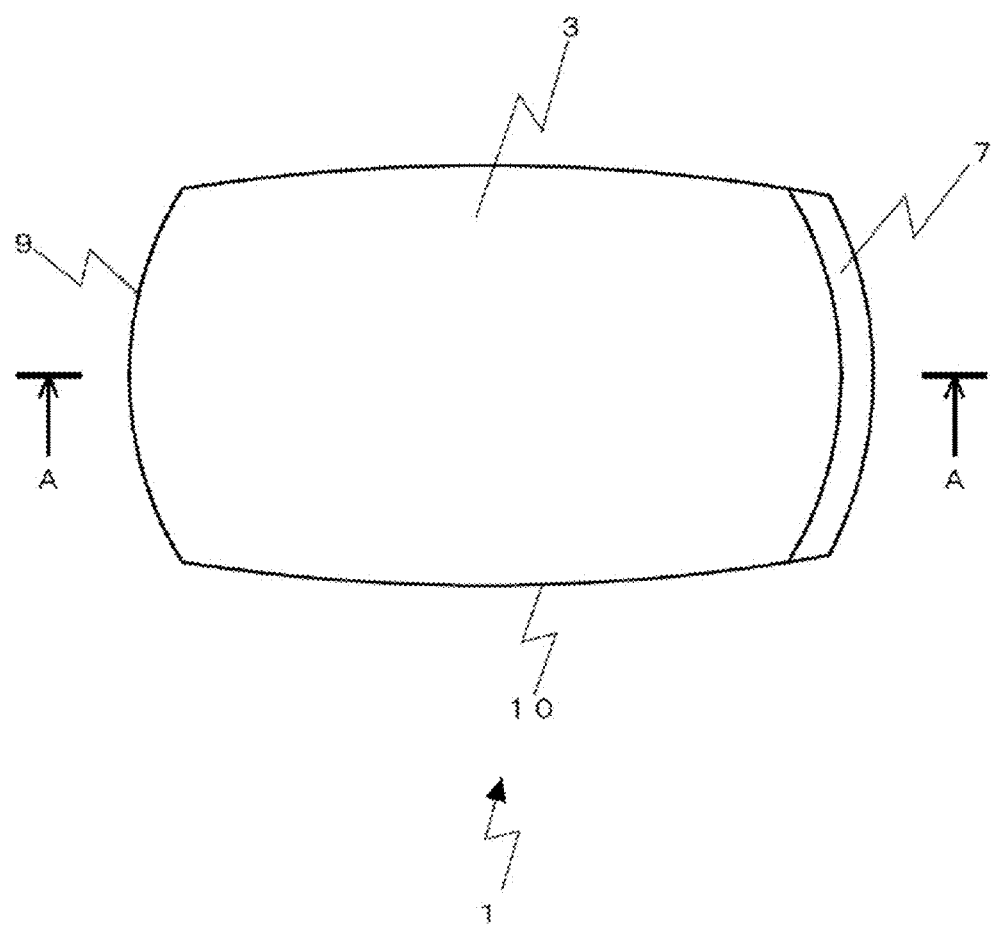

[Fig.4]
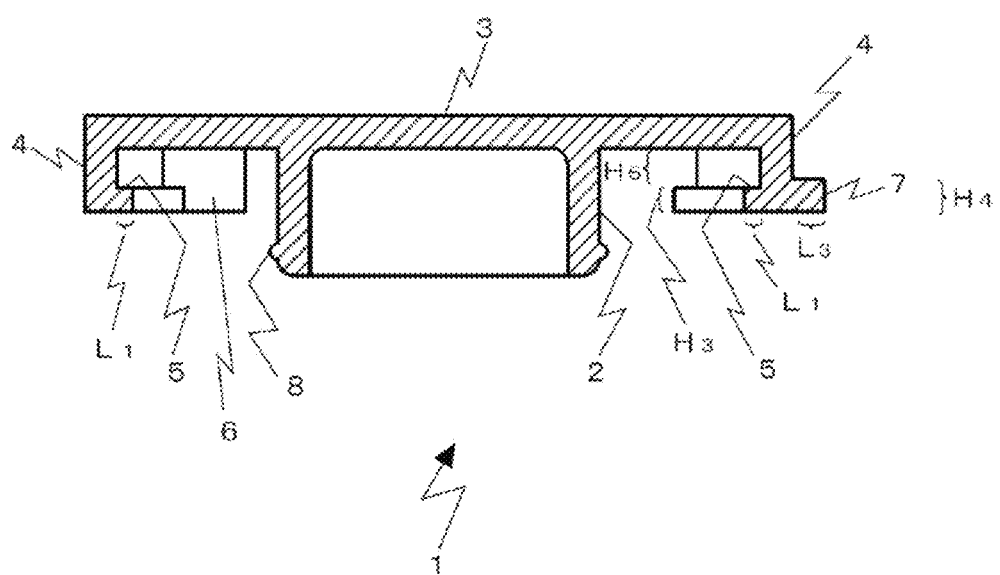

[Fig.5]
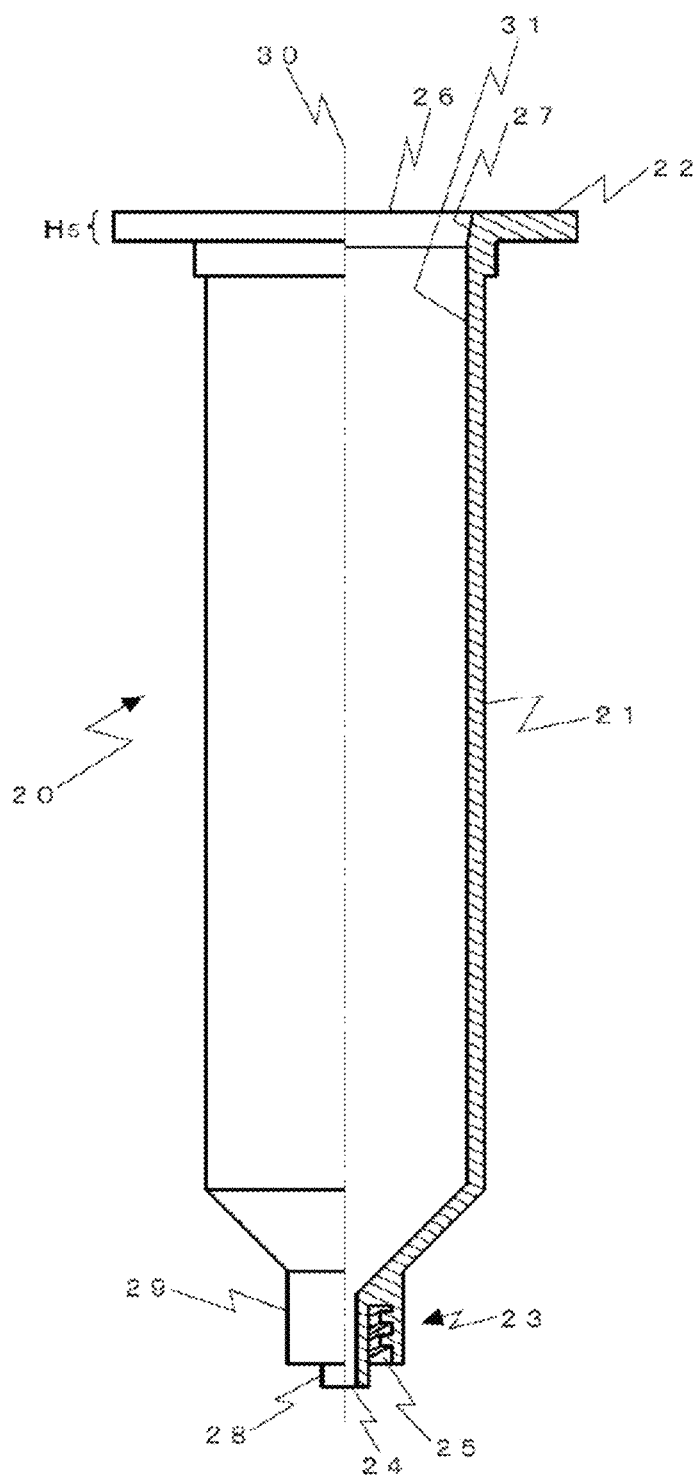

[Fig.6]
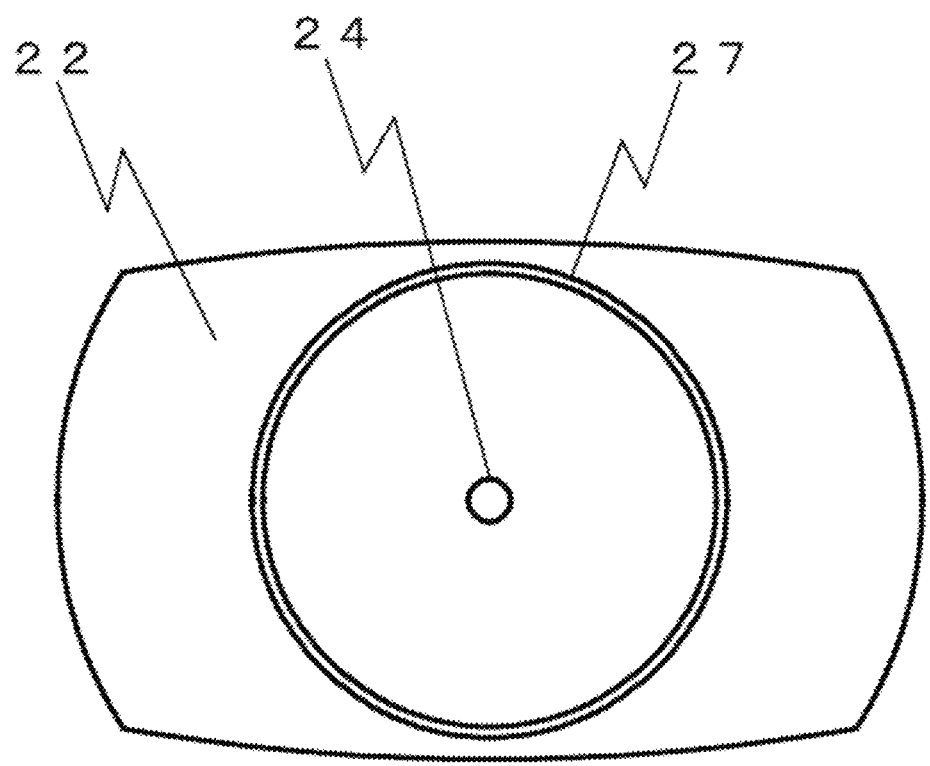

[Fig.7]
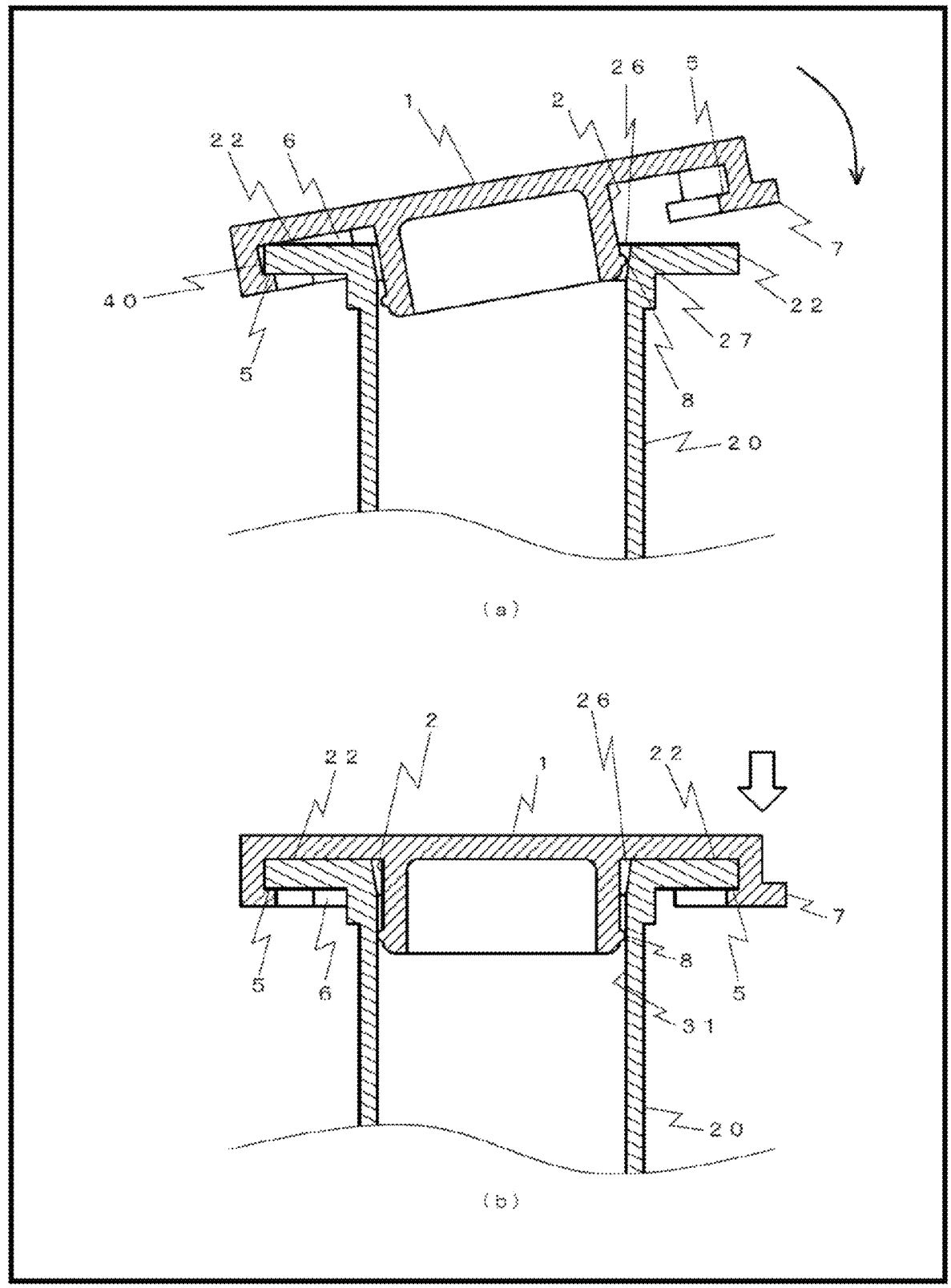

[Fig.8]
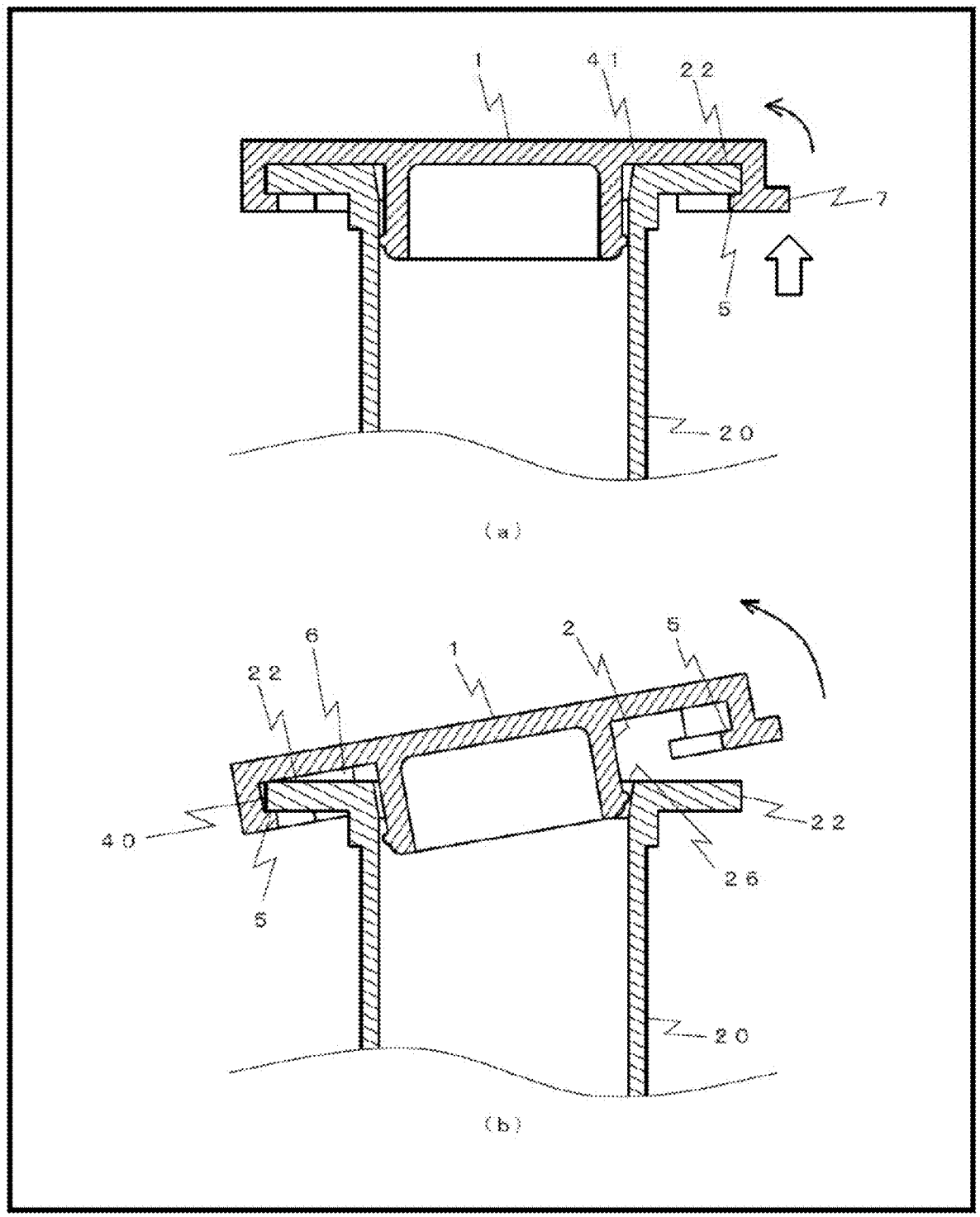

[Fig.9]
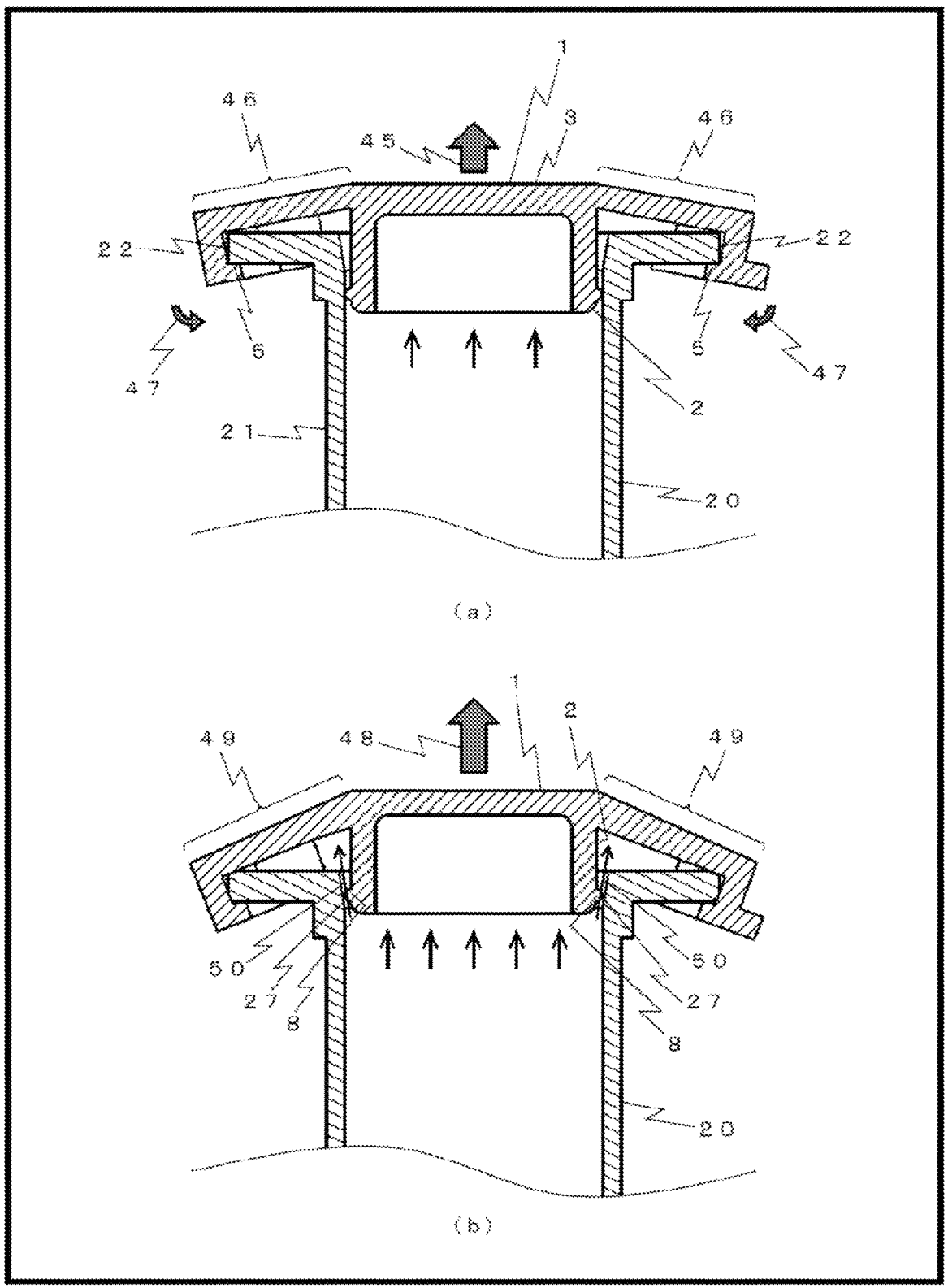

[Fig.10]
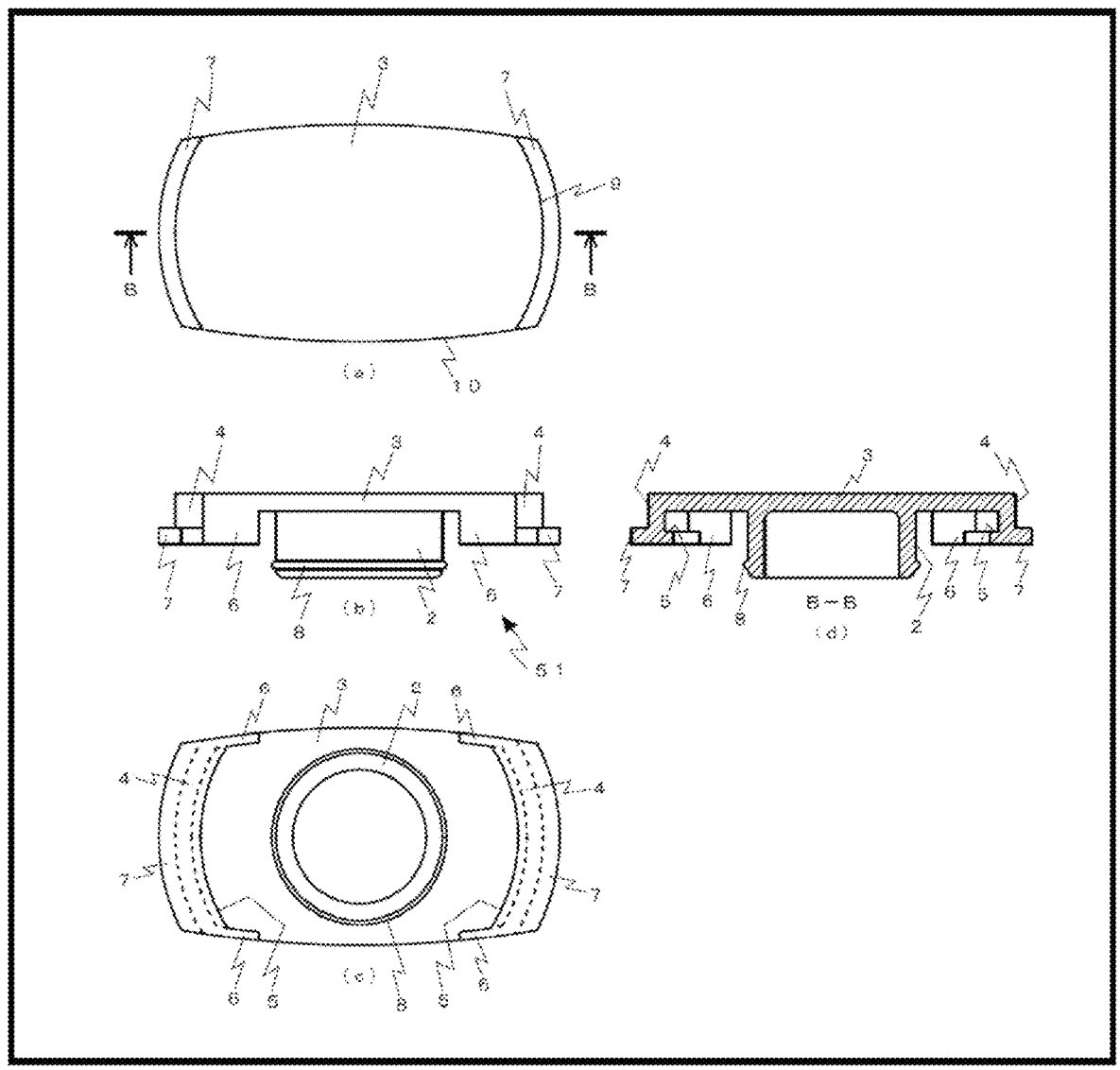

[Fig.11]
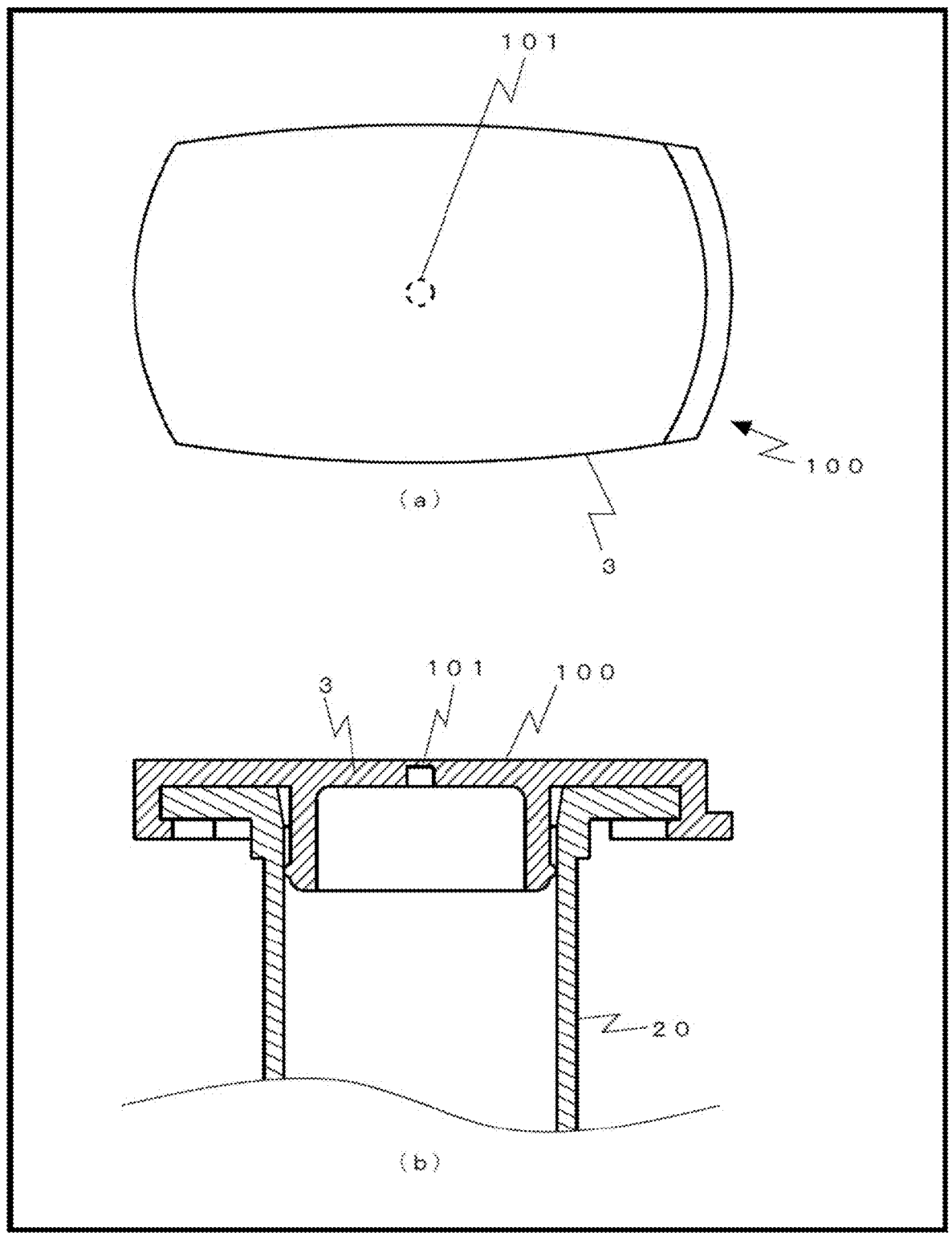

US 11,117,713 B2

LID FOR LIQUID MATERIAL STORAGE CONTAINER, AND LIQUID MATERIAL STORAGE CONTAINER

TECHNICAL FIELD

The present invention relates to a lid for a liquid material storage container and to the liquid material storage container.

BACKGROUND ART

In a liquid material discharge device, the so-called syringe is used as a container for storing a liquid material to be discharged. The syringe is mainly constituted by a cylindrical barrel portion (storage cylinder) in which the liquid material is stored, a flange extending outward in a radial direction from one end of the barrel portion, and an attachment portion formed at an end of the barrel portion on the opposite side to the flange, the attachment portion including a hole in communication with the inside of the barrel portion and a screw portion. The syringe is used in a state in which the liquid material is filled in the barrel portion. In the above-described syringe, lids (caps) are fitted to both ends on the flange side and the attachment-portion side when the syringe is not used or is carried. The following techniques have hitherto been proposed regarding the lid (cap) fitted to the flange side.

Patent Document 1 discloses an injector tube for a dispenser, the injector tube comprising a cylinder (syringe) storing a paste-like composition, a nozzle cap detachably attached to a nozzle portion formed in the cylinder, a head cap detachably attached to the cylinder, and a piston disposed in the cylinder to be freely movable and feeding the paste-like composition under pressure, wherein the head cap includes a ventilation portion for eliminating a pressure difference between the inside and the outside of the cylinder.

Patent Document 2 discloses an endcap or a syringe-type discharge device including a syringe tube that has an open end and a pair of ear portions provided near the open end and arranged in an opposing relation, the endcap comprising an annular flange, first engagement claws and second engagement claws disposed on both sides of the flange, and a flexible central portion formed on the inner side of the flange in a radial direction, the flexible central portion being flexible to deform such that the engagement claws are easily snap-fitted into a state covering the ear portions of the syringe tube.

The applicant also proposes, in Patent Document 3, a plug lid for a liquid material storage container including a storage cylinder having a large-diameter opening at an upper end and a small-diameter opening at a lower end, and a flange extending laterally from an upper end portion of the storage cylinder, the plug lid comprising a base, a plug portion extending downward from substantially a center of the base, and a hook portion provided at a predetermined distance from the center of the base, the plug lid closing the large-diameter opening, wherein the hook portion is constituted by a lateral member extending downward from the base, a flange retention claw extending from the lateral member toward the plug portion, and a flange contact surface formed by a lateral surface of the lateral member on the side from which the flange retention claw extends, the flange contact surface comes into contact with a lateral surface of the flange to specify a turning position of the plug lid relative to the storage container, and the flange retention claw prevents detachment of the plug lid.

CITATION LIST

Patent Documents

Patent Document 1: Japanese Patent Laid-Open Publication No. 2003-175353
Patent Document 2: Japanese National Publication of International Patent Application No. 2009-539607
Patent Document 3: Japanese Patent No. 4986600

SUMMARY OF INVENTION

Technical Problem

The related-art lid for the liquid material storage container has a problem that the lid (cap) may be lifted up due to a pressure rise within the syringe or accidental contact and may come off in the worst case. In the cap of the type disclosed in Patent Document 1, particularly, the above-mentioned problem seems more likely to occur because the cap is held in a fitted state only by friction between an inner peripheral surface of the syringe and an outer peripheral surface of the cap (or a projection formed on the outer peripheral surface).

On the other hand, when trying to firmly engage the lid (cap) with the liquid material storage container by using the claw, there is a problem that a lid body or the claw may be broken, or that efficiency in attachment and detachment operations may deteriorate. The cap of the type disclosed in Patent Document 2 seems to have another problem that, because the engagement claw is long and has a sharp edge, a defect may be caused if the engagement claw is scraped and scraped fragments are mixed into the liquid material when the cap is attached and detached.

In addition, how to improve the efficiency of operations of attaching and detaching the lid for the liquid material storage container is also a problem to be solved by the present invention.

Accordingly, an object of the present invention is to provide a lid for a liquid material storage container, which can solve the problems of uplift and breakage of the lid for the liquid material storage container, and which ensures high efficiency in attachment and detachment operations, and to further provide the liquid material storage container.

Solution to Problem

The present invention provides a lid for a liquid material storage container including a storage cylinder that has a large-diameter opening at an upper end and a small-diameter opening at a lower end, and a flange extending in opposite lateral directions from an upper end portion of the storage cylinder, the lid closing the large-diameter opening, the lid comprising an upper plate portion covering the flange and the large-diameter opening; a plug portion extending downward from a central region of the upper plate portion and plugging the large-diameter opening of the storage cylinder; a pair of first lateral portions coming into contact with lateral surfaces of a pair of short sides of the flange when the lid is closed; a pair of claw portions extending from the pair of first lateral portions toward the plug portion and coming into contact with lower surfaces of the pair of short sides of the flange when the lid is closed; and a push-up operating portion formed in at least one of the pair of first lateral portions, wherein a length of each of the claw portions is shorter than a distance between the claw portion and the upper plate portion.

In the above-described lid for the liquid material storage container, at least the upper plate portion, the pair of first lateral portions, the pair of claw portions, and the push-up operating portion may be integrally formed of a synthetic resin material.

The above-described lid for the liquid material storage container may further comprise a second lateral portion provided in association with one of the first lateral portions, and the second lateral portion may be constituted by a pair of plate-like members extending from both short sides of the pair of first lateral portions toward the plug portion and coming into contact with lateral surfaces of a pair of long sides of the flange.

In the above-described lid for the liquid material storage container, the push-up operating portion may be constituted by a plate-like member extending outward from the first lateral portion on the side where the second lateral portion is not provided.

The above-described lid for the liquid material storage container may further comprise a pair of second lateral portions provided in a one-to-one relation to the pair of first lateral portions, and the second lateral portions in pair are each constituted by a pair of plate-like members extending from both short sides of one of the pair of first lateral portions toward the plug portion and coming into contact with lateral surfaces of a pair of long sides of the flange.

In the above-described lid for the liquid material storage container, the push-up operating portion may be constituted by a plate-like member extending outward from the first lateral portion and may be provided in association with each of the pair of first lateral portions.

In the above-described lid for the liquid material storage container, the second lateral portion or the pair of second lateral portions may be formed in a length allowing the whole of the plug portion to be seen when viewed from front.

In the above-described lid for the liquid material storage container, the pair of claw portions may be engaged with the pair of short sides of the flange when the upper plate portion is pushed down in a state in which one of the claw portions is caught on one of the short sides of the flange and the plug portion is inserted into the large-diameter opening, and engagement between the claw portion on the side where the push-up operating portion is provided and the short side of the flange may be released when the push-up operating portion is pushed up from below by a finger.

In the above-described lid for the liquid material storage container, the length of the claw portion may be shorter than a thickness of the claw portion.

In the above-described lid for the liquid material storage container, the length of the claw portion may be 2 mm or shorter.

The above-described lid for the liquid material storage container may further comprise a seal portion provided on a lateral peripheral surface of the plug portion at a position above a lower end thereof.

In the above-described lid for the liquid material storage container, the upper plate portion may include a thin film portion that is broken when an inner pressure of the storage cylinder rises, thus releasing the inner pressure.

In the above-described lid for the liquid material storage container, the plug portion may be constituted by a tubular member having an opening at a lower end.

In the above-described lid for the liquid material storage container, engagement between the claw portion on the side where the push-up operating portion is provided and the short side of the flange may be released when, in a state of grasping the storage cylinder by one hand, a user pushes up the push-up operating portion from below by the thumb of the hand.

The present invention also provides a liquid material storage container to which the above-described lid for the liquid material storage container is fitted, the liquid material storage container comprising a storage cylinder having a large-diameter opening at an upper end and a small-diameter opening at a lower end, and a flange extending in opposite lateral directions from an upper end portion of the storage cylinder, wherein an expanding portion is formed in an inner peripheral surface of the large-diameter opening.

The present invention further provides a lid-equipped liquid material storage container comprising a storage cylinder having a large-diameter opening at an upper end and a small-diameter opening at a lower end, a flange extending in opposite lateral directions from an upper end portion of the storage cylinder, and the above-described lid for the liquid material storage container, wherein an expanding portion is formed in an inner peripheral surface of the large-diameter opening.

The present invention still further provides a lid-equipped liquid material storage container comprising a storage cylinder having a large-diameter opening at an upper end and a small-diameter opening at a lower end, a flange extending in opposite lateral directions from an upper end portion of the storage cylinder, and the above-described lid for the liquid material storage container, wherein an expanding portion is formed in an inner peripheral surface of the large-diameter opening, and the plug portion is formed in such a length that, when an inner pressure of the storage cylinder rises and the upper plate portion is elastically deformed, the inner pressure is released through the expanding portion before the upper plate portion is broken.

In the lid-equipped liquid material storage container described above, a height of the plug portion may be 1.2 to 2 times a height of the first lateral portion.

In the lid-equipped liquid material storage container described above, a shape of the upper plate portion may be similar to a shape of the flange.

In the lid-equipped liquid material storage container described above, a distance between the claw portion and the upper plate portion may be substantially equal to a thickness of the flange.

Advantageous Effects of Invention

According to the present invention, the problems of uplift and breakage of the lid for the liquid material storage container can be solved. In addition, the lid for the liquid material storage container and the liquid material storage container can be obtained each of which ensures high efficiency in lid attachment and detachment operations.

BRIEF DESCRIPTION OF THE DRAWINGS

FIG. 1 is a front view of a lid according to a first embodiment.

FIG. 2 is a bottom view of the lid according to the first embodiment.

FIG. 3 is a plan view of the lid according to the first embodiment.

FIG. 4 is a sectional view of the lid cut along a line A-A in FIG. 3.

FIG. 5 represents a front view and a sectional view of a liquid material storage container using the lid according to the first embodiment.

FIG. 6 is a plan view of the liquid material storage container using the lid according to the first embodiment.

FIG. 7 is an explanatory view referenced to explain operation of attaching the lid according to the first embodiment to the liquid material storage container. In FIG. 7, (a) represents a state in which a plug portion starts to engage with a storage cylinder, and (b) represents a state in which the lid is closed.

FIG. 8 is an explanatory view referenced to explain an operation of detaching the lid according to the first embodiment from the liquid material storage container. In FIG. 8, (a) represents a state in which a push-up operating portion is going to be pushed up, and (b) represents a state in which the lid is opened.

FIG. 9 is an explanatory view referenced to explain an action of releasing gas from the lid according to the first embodiment. In FIG. 9, (a) represents a state in which an upper plate portion is deformed due to an inner pressure of the container, and (b) represents a state in which the upper plate portion is further deformed and an annular projection of the plug portion departs away from an inner wall of the storage cylinder, whereupon the inner pressure is released.

FIG. 10 is an explanatory view of a lid according to a second embodiment. In FIG. 10, (a) is a plan view, (b) is a front view, (c) is a bottom view, and (d) is a sectional view of the lid cut along a line B-B in (a).

FIG. 11 is an explanatory view of a lid according to a third embodiment. In FIG. 11, (a) is a plan view and (b) is a sectional view.

DESCRIPTION OF EMBODIMENTS

Embodiments for carrying out the present invention will be described below.

First Embodiment (1) Structure of Lid 1

As illustrated in FIGS. 1 to 4, a lid 1 according to a first embodiment is constituted by a plug portion 2, an upper plate portion 3, first lateral portions 4, claw portions 5, a second lateral portion 6, and a push-up operating portion 7. In the following description, the side closer to the upper plate portion 3 than the plug portion 2 is called the "upper side" and the side closer to the plug portion 2 than the upper plate portion 3 is called the "lower side" in some cases.

The plug portion 2 is a cylindrical member extending in a vertical direction and is joined at its upper end to a lower surface of the upper plate portion 3. An annular projection 8 is formed on an outer peripheral surface of the plug portion 2 near a lower end, and it comes into contact with an inner wall surface 31 of a storage container 20, thus serving as a seal. The plug portion 2 is hollow and is opened at a lower end. Because a sidewall of the plug portion 2 is thin to be elastically deformable, the plug portion 2 can easily be attached to and detached from a storage cylinder 21 even with an outer diameter of the plug portion 2 being set substantially the same as an inner diameter of the storage cylinder 21. Furthermore, when an inner pressure of the storage cylinder 21 is applied to the opening of the plug portion 2, an action of increasing sealing force is obtained because the sidewall of the plug portion 2 is pressed against the inner wall surface 31.

A height (H2) of the plug portion 2 is just required to be set such that the lower end of the plug portion 2 does not hit against an inner peripheral surface of a large-diameter opening 26 of the storage container 20 when the lid is turned in later-described attachment and detachment operations. However, the height (H2) is desired to be relatively short from the viewpoint of the later-described pressure release action. It is disclosed here, by way of example, that the height (H2) is 1.2 to 2 times or 1.5 to 2 times a height (H1) of the first lateral portion 4.

The upper plate portion 3 extends outward in a radial direction from a lateral edge of the plug portion 2 at the upper end thereof. Because the upper plate portion 3 is in the form of a plate having substantially rectangular shape (FIG. 3) when viewed from above and being elongate with a pair of short sides 9 each having the shape of a partial arc (of an ellipse), the upper plate portion 3 can also be said as having a boat-like shape. The shape of the upper plate portion 3 is similar to that of a flange 22 of the storage container 20, but a size of the upper plate portion 3 is slightly larger than that of the flange 22 because the upper plate portion 3 includes the later-described first and second lateral portions (4 and 6). The lower surface of the upper plate portion 3 comes into contact with an upper surface of the flange 22 of the storage container 20 when the lid is closed.

The first lateral portions 4 are constituted by plate-like members extending downward (in the vertical direction) from ends of the short sides 9 of the upper plate portion 3, respectively. When viewed from above, each of the first lateral portions 4 has the shape of a partial arc (of an ellipse). The height (H1) of the first lateral portion 4 is equal to the sum of a thickness of the upper plate portion 3, a thickness (H5) of the flange 22 of the storage container 20, and a thickness (H3) of the later-described claw portion 5. On the other hand, a width (W1) of the first lateral portion 4 is the same as that of the short side 9 of the upper plate portion 3. As denoted by a dotted line in FIG. 2, an inner lateral surface of the first lateral portion 4 has the shape of a partial arc (of an ellipse) and comes into contact with a short side of the flange 22 of the storage container 20 at a lateral surface thereof when the lid is closed.

The claw portions 5 are plate-like members extending in a horizontal direction, and they extend from lower ends of the first lateral portions 4 and 4 toward the plug portion 2. Each of the claw portions 5 has a similar shape to that of the first lateral portion 4, i.e., the shape of a partial arc (of an ellipse), when viewed from bottom. As illustrated in FIG. 4, a length (L1) of the claw portion 5 may be short just enough to make the claw portion 5 caught on the flange 22 of the storage container 20. For example, the length (L1) is set to fall within a range of 2 mm or shorter (preferably 0.1 to 1.5 mm and more preferably 0.15 to 1 mm). From another point of view, the length (L1) of the claw portion 5 is just required to be shorter than the thickness (H3) of the claw portion. It is disclosed here, by way of example, that the length (L1) is set to 1/20 to 3/4, more preferably 1/10 to 3/4, and even more preferably 1/5 to 2/3 of the thickness (H3) of the claw portion.

On the other hand, a width of the claw portion 5 is substantially the same as that (W1) of the first lateral portion 4. An upper surface of the claw portion 5 comes into contact with a lower surface of the flange 22 of the storage container 20 when the lid is closed. In this embodiment, a distance between the claw portion 5 and the upper plate portion 3 is equal to the thickness (H5) of the flange 22. The distance between the claw portion 5 and the upper plate portion 3 is to be longer than the length (L1) of the claw portion 5 and is, for example, 3 to 12 times the length (L1) of the claw portion 5. When the upper plate portion 3 is pushed down in a state in which one claw portion 5 is caught on one short side of the flange 22 and the plug portion 2 is inserted into the large-diameter opening 26, the pair of claw portions 5 and 5 are engaged with the pair of short sides of the flanges 22 and 22, respectively, whereby the lid is closed. When the lid is opened, the engagement between the claw portion 5 on the same side as the push-up operating portion 7 and the short side of the flange 22 is released by pushing the push-up operating portion 7 upward from below by a finger.

The second lateral portion 6 is constituted by a pair of plate-like members extending in the vertical direction. The second lateral portion 6 is provided in continuity with two short sides of the first lateral portion 4 (i.e., two short sides illustrated in FIG. 2 near positions denoted by L2). When viewed from bottom, the second lateral portion 6 extends from the two short sides (two ends) of the first lateral portion 4 toward the central region of the upper plate portion 3 along its long sides 10. In the first embodiment, the second lateral portion 6 is provided in association with only one of the two first lateral portions 4. Although a length (L2) of the second lateral portion 6 is required to have a size just enough to develop the later-described guide function and rotation stop function, it is disclosed here, by way of example, that the length (L2) is set to such a length as allowing the whole of the plug portion 2 to be seen when viewed from front, or that the length (L2) is not longer than ¼ or ⅙ of that of the long side 10 of the upper plate portion 3. In other words, the second lateral portion 6 and the first lateral portion 4 are constituted to provide a bracket-like ("[" or "]") shape or a substantially C-like shape when viewed from bottom. A height of the second lateral portion 6 is equal to that of the first lateral portion 4. When the lid is closed, the second lateral portion 6 comes into contact with parts of long sides of the flange 22 of the storage container 20 at a lateral surface thereof.

The push-up operating portion 7 is a plate-like member extending outward in a lengthwise direction of the upper plate portion 3 from the first lateral portion 4 on the side different from the side where the second lateral portion 6 is provided. The push-up operating portion 7 serves as a portion that is operated to be pushed up to detach the lid 1. As the push-up operating portion 7 is projected through a larger distance from the first lateral portion 4, force needed for the operation of pushing up the push-up operating portion 7 decreases. However, if a projection amount (L3) of the push-up operating portion 7 is too large, the push-up operating portion 7 disturbs carrying the lid. Thus, the projection amount (L3) is set to an appropriate value. In the first embodiment, the projection amount (L3) of the push-up operating portion 7 from the first lateral portion 4 is set to be substantially the same as a thickness of the push-up operating portion 7. In FIG. 2, an innermost edge of the push-up operating portion 7 is denoted by a dotted line.

In the first embodiment, a width of the push-up operating portion 7 is the same as that (W1) of the first lateral portion 4 and that of the short side 9 of the upper plate portion. However, the width of the push-up operating portion 7 is not always required to be the same as that (W1) of the first lateral portion 4, and the push-up operating portion 7 having a shorter width than that (W1) of the first lateral portion 4 may be provided in a central region of the short side 9 of the upper plate portion. Although the lid 1 can also be detached in the case of not providing the push-up operating portion 7, easiness in detaching the lid 1 lowers in that case.

While, in the first embodiment, the push-up operating portion 7 extends from the lower end of the first lateral portion 4, the present invention is not limited to such a structure. In another example, the push-up operating portion 7 may be provided to extend in the horizontal direction from an upper end of the first lateral portion 4 or an intermediate position between the upper and lower ends thereof. A height (H4) of the push-up operating portion 7 is just required to give the push-up operating portion 7 with such a thickness that the push-up operating portion 7 is not excessively deformed when pushed up to detach the lid 1. For example, the height (H4) is set to fall within a range from the thickness (H3) of the claw portion to the height (H1) of the first lateral portion 4. From another point of view, the push-up operating portion 7 may be constituted by increasing a thickness of the first lateral portion 4 in the horizontal direction in its part along the height (H1) by a distance corresponding to the projection amount (L3).

While, in the first embodiment, either one of the second lateral portion 6 and the push-up operating portion 7 is provided on one of the opposite sides with the plug portion 2 interposed therebetween, both the second lateral portion 6 and the push-up operating portion 7 may be disposed on each of the opposite sides with the plug portion 2 interposed therebetween as described later (FIG. 10).

The lid 1 according to the first embodiment is made of an elastically-deformable (thermoplastic) synthetic resin material (such as polypropylene, polyethylene, polycarbonate, polyurethane, polyamide, or polystyrene). In the first embodiment, individual elements constituting the lid 1 (namely, the plug portion 2, the upper plate portion 3, the first lateral portions 4, the claw portions 5, the second lateral portion 6, and the push-up operating portion 7) are formed integrally together.

(2) Structure of Liquid Material Storage Container 20

The lid 1 according to the first embodiment is used for the liquid material storage container 20 illustrated in FIGS. 5 and 6. The liquid material storage container 20 is a container mainly constituted by the cylindrical storage cylinder 21 in which a liquid is stored, the flange 22 extending outward in the radial direction from an end portion (upper end portion) of the storage cylinder 21 on the side where the large-diameter opening 26 is located, and an attachment portion 23 to which a nozzle or a nozzle cap is attached, the attachment portion 23 being formed in an end portion (lower end portion) of the storage cylinder 21 on the opposite side to the flange 22. In FIG. 5, a sectional view is illustrated on the right side of a center line 30, and a front view is illustrated on the left side. The liquid material storage container 20 is designed in various storage amounts such as 5 cc, 10 cc, 30 cc, and 50 cc, for example.

The large-diameter opening 26 is formed at the end portion of the storage cylinder 21 on the side where the flange 22 is disposed. The inner peripheral surface of the large-diameter opening 26 includes an expanding portion 27 of which diameter gradually increases toward the side away from the attachment portion 23. With the presence of the expanding portion 27, the plug portion 2 of the lid 1, a not-illustrated adaptor used to supply compressed gas, etc. can be more easily fitted to the storage container 20. In addition, the expanding portion 27 is further required to realize the later-described pressure release action.

The attachment portion 23 includes a small-diameter opening 24 in communication with an inner space of the storage cylinder 21, a screw portion 25, an inner cylinder 28, and an outer cylinder 29. The small-diameter opening 24 is formed in the inner cylinder 28 having a tubular shape. The outer cylinder 29 surrounds the inner cylinder 28, and the screw portion 25 is formed in an inner peripheral surface of the outer cylinder 29. When the storage container 20 is carried or kept in a storage place, a similar lid (cap) to that in the related art is attached to be screwed into the screw portion 25. (See the nozzle cap disclosed in Patent Document 1. Detailed description of such a lid is omitted here.)

(3) Attachment and Detachment Operations

The lid 1 according to the first embodiment is attached to the liquid material storage container 20 by an operation described below. First, as illustrated in FIG. 7(a), the claw portion 5 on the side where the second lateral portion 6 is provided catches the flange 22 of the storage container 20, and the upper plate portion 3 is pushed down to be turned with a point, denoted by reference numeral 40, being a center (fulcrum) such that a region of the upper plate portion 3 on the side closer to the push-up operating portion 7 approaches the flange 22 of the storage container 20. With that push-down operation, the annular projection 8 of the plug portion 2 comes into contact with the inner peripheral surface (expanding portion 27) of the large-diameter opening 26 of the storage container 20 and starts to engage therewith before the claw portion 5 on the same side as the push-up operating portion 7 is engaged with the flange 22 of the storage container 20. The height of the plug portion 2 is set such that the lower end of the plug portion 2 does not hit against the inner peripheral surface (expanding portion 27) of the large-diameter opening 26 of the storage container 20. At that time, because the two members of the second lateral portion 6 are held in contact with the long sides of the flange 22 of the storage container 20 in a sandwiching relation, they serve as a guide for guiding the whole of the lid 1 not to be slipped off from the flange 22 of the storage container 20. In addition, when the lid is closed, the second lateral portion 6 can firmly hold the flange 22 of the storage container 20 in cooperation with the first lateral portions 4, and can serve as a rotation stopper to prevent the lid 1 from rotating about an axis denoted by reference numeral 30 (see FIG. 5). Then, by further applying force to push down the upper plate portion 3 on the side close to the push-up operating portion 7, as illustrated in FIG. 7(b), the claw portions 5 are both engaged with the flange 22 of the storage container 20 due to elastic deformation of the lid 1 itself, whereby the operation of attaching the lid (i.e., closing the lid) is completed. At the same time, the plug portion 2 is completely fitted to the large-diameter opening 26 of the storage container 20. Furthermore, the annular projection 8 of the plug portion 2 comes into contact with the inner wall surface 31 of the storage container 20, thus ensuring positive sealing. Since the claw portion 5 is short and the deformation of the lid 1 itself is small, the force required to be applied to the upper plate portion 3 is small.

On the other hand, the lid 1 according to the first embodiment is detached from the liquid material storage container 20 by an operation described below. First, as denoted by an arrow in FIG. 8(a), when force is applied to push up the push-up operating portion 7 from below, a region of the upper plate portion 3 on the side closer to the push-up operating portion 7 than a point denoted by reference numeral 41 is turned (raised) with the point 41 being a center, whereby the engagement between the claw portion 5 on the same side as the push-up operating portion 7 and the flange 22 of the storage container 20 is released. This is effectuated by elastic deformation of the lid 1 itself. However, since the claw portion 5 is short and the deformation of the lid 1 is small, the force required to be applied to the push-up operating portion 7 is small. As illustrated in FIG. 8(b), when the force is continuously applied to the push-up operating portion 7, the whole of the lid 1 is turned with the point, denoted by reference numeral 40, being a center in a state in which the claw portion 5 on the side where the second lateral portion 6 is provided is caught on the flange 22 of the storage container 20. Then, the plug portion 2 is withdrawn from the large-diameter opening 26 of the storage container 20 and the whole of the lid 1 is detached. Thus, the operation of detaching the lid (i.e., opening the lid) is completed. At that time, as in the attachment operation, because the two members of the second lateral portions 6 are held in contact with the long sides of the flange 22 of the storage container 20 in a sandwiching relation, they serve as a guide for guiding the whole of the lid 1 not to be slipped off from the flange 22 of the storage container 20.

Since the lid 1 can be attached or detached (i closed or opened) just by applying the force to push down or up the push-up operating portion 7 as described above, the operation of attaching or detaching the lid can easily be performed by one hand. In other words, a user can attach and detach the lid 1 by operating the push-up operating portion 7 with the thumb in a state of grasping the storage cylinder 21 with the other four fingers.

As described above, since the lid 1 according to the first embodiment is constituted such that the claw portions 5 have the length with which the user can attach and detach the lid 1 just by manually applying the force, and that the plug portion 2 has the height with which the lower end of the plug portion 2 can be kept from hitting against the inner peripheral surface (expanding portion 27) of the large-diameter opening 2 of the storage container 20, the lid can easily be attached and detached. Furthermore, since the second lateral portion is provided to serve as the guide, the lid can be attached and detached without being displaced.

Moreover, since the claw portion is set to be short just enough to enable the user to attach and detach the lid by manually applying the force, it is possible to suppress generation of scraped fragments, and to prevent troubles that may occur with mixing of the scraped fragments into the liquid material.

(4) Pressure Release Action

Even if a pressure within the liquid material storage container 20 excessively rises with evaporation of the liquid material, reduction of the ambient atmospheric pressure, etc., the lid 1 according to the first embodiment can be avoided due to the pressure release action, described below, from being removed without being artificially operated.

As illustrated in FIG. 9(a), when the pressure within the storage container 20 rises, the pressure is applied to a top surface of the plug portion 2 (lower surface of the upper plate portion 3 in the central region), and the plug portion 2 is lifted up (as denoted by reference numeral 45). Accordingly, regions of the upper plate portion 3 on the outer side than the plug portion 2 are deformed to expand (as denoted by reference numeral 46). At that time, the claw portions 5 are moved to be pushed toward the storage cylinder 21 of the storage container 20 (as denoted by reference numeral 47), and their movements act in a direction of strengthening the engagement with the flange 22. Thus, the lid 1 is not removed even when the pressure within the storage container 20 rises.

As illustrated in FIG. 9(b), when the pressure within the storage container 20 further rises, the plug portion 2 is further lifted up (as denoted by reference numeral 48), and the regions of the upper plate portion 3 on the outer side than the plug portion 2 are further expanded (as denoted by reference numeral 49). At that time, when the annular projection 8 of the plug portion 2 comes into the expanding portion 27 formed in the inner peripheral surface of the large-diameter opening 26 of the storage container 20, a gap is formed between the annular projection 8 of the plug portion 2 and the inner wall of the storage container 20, and part of gas in the storage container 20 is released through the gap (as denoted by reference numeral 50). With the release of the gas inside the storage container 20, the pressure within the storage container 20 drops. As a result, the force acting to lift up the plug portion 2 reduces, and the lid 1 returns to the original state (see FIG. 7(b)) or the state illustrated in FIG. 9(a) due to elasticity of the lid 1 itself.

The magnitude of the pressure within the storage container 20 at the timing of the pressure release can be adjusted by changing the height of the plug portion 2. However, attention is to be paid such that the height of the plug portion 2 is not to be set so high as to cause troubles in the above-described attachment and detachment operations.

Thus, since the pressure release action is realized in the lid 1 according to the first embodiment, the lid can be avoided from being accidentally removed from the storage container. Furthermore, the action of releasing the pressure within the storage container 20 prevents the lid 1 from excessively deforming beyond a limit and from being broken.

Second Embodiment

A lid 51 according to a second embodiment is different from the lid according to the first embodiment in having a symmetric structure in which the push-up operating portion 7 and the second lateral portion 6 are both provided at each of opposite ends of the upper plate portion 3 extending horizontally. In the following, different points from the first embodiment are mainly described, and description of common components is omitted.

Unlike the lid 1 according to the first embodiment, the lid 51 according to the second embodiment includes, as illustrated in FIG. 10, the push-up operating portion 7 and the second lateral portion 6 that are provided at the end of each of the first lateral portions 4. In other words, the lid 51 according to the second embodiment has a symmetric shape with respect to the plug portion 2 being a center. The plug portion 2, the upper plate portion 3, the first lateral portions 4, and the claw portions 5 are the same as those in the first embodiment, and description of those components is omitted.

The operations of attaching and detaching the lid to and from the storage container 20 are basically similar to those in the first embodiment. However, because the push-up operating portion 7 and the second lateral portion 6 are both provided at each of the opposite ends of the upper plate portion 3, the attachment and detachment operations can be performed on either side regardless of direction. More specifically, the lid 51 can be attached (closed) by making the claw portion 5, which is provided on any one of the two short sides of the lid 51, caught on the flange 22 of the storage container 20, and the lid 51 can be detached (opened) by pushing up either one of the two short sides of the lid 51.

Furthermore, the lid 51 according to the second embodiment can also of course realize the pressure release action because the plug portion 2, the upper plate portion 3, the first lateral portions 4, and the claw portions 5 are similar to those in the first embodiment.

Thus, the lid 51 according to the second embodiment can also provide similar advantageous effects to those obtained with the lid 1 according to the first embodiment.

Moreover, the lid 51 according to the second embodiment is more convenient in use because the lid 51 can be attached and detached by operating the lid on either side including one of the two short sides of the lid 51.

Third Embodiment

A lid 100 according to a third embodiment is different from the lid according to the first embodiment in including a breakable pressure release mechanism as means for releasing the pressure within the liquid material storage container 20 when the lid is in the closed state. In the following, different points from the first embodiment are mainly described, and description of common components is omitted.

In the lid 100 according to the third embodiment, as illustrated in FIG. 11, the pressure release mechanism is constituted by forming, in the top surface of the plug portion 2, a thin film portion 101 having a thickness thinner than other regions around the thin film portion 101. The plug portion 2, the upper plate portion 3, the first lateral portions 4, and the claw portions 5 are the same as those in the first embodiment, and description of those components is omitted.

If the pressure within the liquid material storage container 20 excessively rises with evaporation of the liquid material, reduction of the ambient atmospheric pressure, etc. when the lid is closed, the thin film portion 101 is broken and the inner pressure is released. The magnitude of the pressure at the timing of the pressure release can be adjusted by changing the thickness of the thin film portion 101. The feature of the thin film portion 101 may be effectuated in combination with the action described in the first embodiment, i.e., the action that the plug portion is lifted up to strengthen the engagement between each of the claw portions 5 and the flange 22 (see FIG. 9(a)). The diameter and the thickness of thin film portion 101 may be, for example, about 1 mm and about several tens μm, respectively.

While, in the third embodiment, the thin film portion 101 is constituted to form a surface in flush with the upper surface of the upper plate portion 3, the present invention is not limited to such a structure, and the thin film portion 101 may be constituted to form a surface in flush with the lower surface of the upper plate portion 3, or constituted to position between the upper and lower surfaces of the upper plate portion 3.

With the above-described structure, the lid 100 can be avoided from being accidentally removed from the storage container. Moreover, with the pressure release action, any other portion of the lid than the thin film portion 101 is prevented from excessively deforming beyond a limit and from being broken. When a floating plunger (floating piston) is disposed, the liquid material can be kept from flowing out through the thin film portion 101 after being broken.

While the preferred embodiments of the present invention have been described above, the technical scope of the present invention is not limited to the matters described in the above embodiments. The above embodiments can be variously modified and improved, and the modified and improved embodiments also fall within the technical scope of the present invention.

LIST OF REFERENCE SIGNS

1: lid according to first embodiment, 2: plug portion, 3: upper plate portion, 4: first lateral portion, 5: claw portion, 6: second lateral portion, 7: push-up operating portion, 8: annular projection (seal portion), 9: short side of upper plate portion, 10: long side of upper plate portion, 20: storage container, 21: storage cylinder, 22: flange, 23: attachment portion, 24: small-diameter opening, 25: screw portion, 26: large-diameter opening, 27: expanding portion, 28: inner cylinder, 29: outer cylinder, 30: center line, 31: inner wall surface, 40: first turning center, 41: second turning center, 45: lift-up of plug portion, 46: deformation of upper plate portion, 47: push-in of claw portion, 48: lift-up of plug portion, 49: deformation of upper plate portion, 50: gas release, 51: lid according to second embodiment, H1: height of first lateral portion, H2: height of plug portion, H3: thickness of claw portion, H4: height of push-up operating portion, H5: thickness of flange, L1: length of claw portion, L2: length of second lateral portion, 100: lid according to third embodiment, 101: thin film portion

The invention claimed is:

1. A lid for a liquid material storage container including a storage cylinder that has a first opening at an upper end and a second opening at a lower end, and a flange extending in opposite lateral directions from an upper end portion of the storage cylinder, the lid closing the first opening, the first opening having a diameter larger than a diameter of the second opening, the lid comprising:
an upper plate portion covering the flange and the first opening;
a plug portion extending downward from a central region of the upper plate portion and plugging the first opening of the storage cylinder;
a pair of first lateral portions coming into contact with lateral surfaces of a pair of short sides of the flange when the lid is closed;
a pair of claw portions extending from the pair of first lateral portions toward the plug portion and coming into contact with lower surfaces of the pair of short sides of the flange when the lid is closed;
a second lateral portion provided in association with one of the first lateral portion; and
a push-up operating portion formed in at least one of the pair of first lateral portions,
wherein a length of each of the claw portions is shorter than a distance between the claw portion and the upper plate portion, and
wherein the second lateral portion is constituted by a pair of plate-shaped members extending from both short sides of the pair of first lateral portions toward the plug portion and coming into contact with lateral surfaces of a pair of long sides of the flange.

2. The lid for the liquid material storage container according to claim 1, wherein at least the upper plate portion, the pair of first lateral portions, the second lateral portion, the pair of claw portions, and the push-up operating portion are integrally formed of a synthetic resin material.

3. The lid for the liquid material storage container according to claim 1, wherein the push-up operating portion is constituted by a plate-shaped member extending outward from the first lateral portion on the side where the second lateral portion is not provided.

4. The lid for the liquid material storage container according to claim 2, further comprising a pair of second lateral portions provided in a one-to-one relation to the pair of first lateral portions,
wherein the second lateral portions in pair are each constituted by a pair of plate-shaped members extending from both short sides of one of the pair of first lateral portions toward the plug portion and coming into contact with lateral surfaces of a pair of long sides of the flange.

5. The lid for the liquid material storage container according to claim 4, wherein the push-up operating portion is constituted by a plate-shaped member extending outward from the first lateral portion and is provided in association with each of the pair of first lateral portions.

6. The lid for the liquid material storage container according to claim 1, wherein the second lateral portion or the pair of second lateral portions are formed in a length allowing the whole of the plug portion to be seen when viewed from front.

7. The lid for the liquid material storage container according to claim 1, wherein the pair of claw portions are engaged with the pair of short sides of the flange when the upper plate portion is pushed down in a state in which one of the claw portions catches one of the short sides of the flange and the plug portion is inserted into the first opening, and
engagement between the claw portion on the side where the push-up operating portion is provided and the short side of the flange is released when the push-up operating portion is pushed up from below by a finger.

8. The lid for the liquid material storage container according to claim 1, wherein the length of the claw portion is shorter than a thickness of the claw portion.

9. The lid for the liquid material storage container according to claim 7, wherein the length of the claw portion is 2 mm or shorter.

10. The lid for the liquid material storage container according to claim 1, further comprising a seal portion provided on a lateral peripheral surface of the plug portion at a position above a lower end thereof.

11. The lid for the liquid material storage container according to claim 1, wherein the upper plate portion includes a thin film portion that is broken when an inner pressure of the storage cylinder rises, thus releasing the inner pressure.

12. The lid for the liquid material storage container according to claim 1, wherein the plug portion is constituted by a tubular member having an opening at a lower end.

13. The lid for the liquid material storage container according to claim 1, wherein engagement between the claw portion on the side where the push-up operating portion is provided and the short side of the flange is released when, in a state of grasping the storage cylinder by one hand, a user pushes up the push-up operating portion from below by the thumb of the hand.

14. A liquid material storage container to which the lid for the liquid material storage container according to claim 10 is fitted, the liquid material storage container comprising:
a storage cylinder having the first opening at an upper end and the second opening at a lower end, and the flange extending in opposite lateral directions from an upper end portion of the storage cylinder,
wherein an expanding portion is formed in an inner peripheral surface of the first opening.

15. A lid-equipped liquid material storage container comprising:
a storage cylinder having the first opening at an upper end and the second opening at a lower end,
the flange extending in opposite lateral directions from an upper end portion of the storage cylinder, and
the liquid material storage container according to claim 10, wherein an expanding portion is formed in an inner peripheral surface of the first opening.

16. A lid-equipped liquid material storage container comprising:
a storage cylinder having the first opening at an upper end and the second opening at a lower end,
the flange extending in opposite lateral directions from an upper end portion of the storage cylinder, and
the liquid material storage container according to claim 11,
wherein an expanding portion is formed in an inner peripheral surface of the first opening, and
the plug portion is formed in such a length that, when an inner pressure of the storage cylinder rises and the upper plate portion is elastically deformed, the inner pressure is released through the expanding portion before the upper plate portion is broken.

17. The lid-equipped liquid material storage container according to claim 15, wherein a height of the plug portion is 1.2 to 2 times a height of the first lateral portion.

18. The lid-equipped liquid material storage container according to claim 15, wherein a shape of the upper plate portion is similar to a shape of the flange.

19. The lid-equipped liquid material storage container according to claim 15, wherein a distance between the claw portion and the upper plate portion is substantially equal to a thickness of the flange.

* * * * *